(12) United States Patent
Stanczak et al.

(10) Patent No.: US 7,901,398 B2
(45) Date of Patent: *Mar. 8, 2011

(54) FAILSAFE RECONFIGURABLE SURGICAL APPARATUS

(76) Inventors: George Stanczak, Park Ridge, IL (US); David Feng, Arlington Heights, IL (US)

( * ) Notice: Subject to any disclaimer, the term of this patent is extended or adjusted under 35 U.S.C. 154(b) by 912 days.

This patent is subject to a terminal disclaimer.

(21) Appl. No.: 10/968,816

(22) Filed: Oct. 20, 2004

(65) Prior Publication Data

US 2005/0131396 A1  Jun. 16, 2005

Related U.S. Application Data

(63) Continuation-in-part of application No. 10/027,343, filed on Dec. 19, 2001, now Pat. No. 7,122,028.

(51) Int. Cl.
*A61B 17/00* (2006.01)

(52) U.S. Cl. ............................................... 606/1; 606/46

(58) Field of Classification Search .................. 606/142, 606/1, 45–52, 205–207
See application file for complete search history.

(56) References Cited

U.S. PATENT DOCUMENTS

| | | | |
|---|---|---|---|
| 5,211,655 A | 5/1993 | Hasson | |
| 5,290,308 A | 3/1994 | Knight et al. | |
| 5,304,203 A | 4/1994 | El-Mallawany et al. | |
| 5,358,508 A | 10/1994 | Cobb | |
| 5,478,347 A | 12/1995 | Aranyi | |
| 5,478,351 A | 12/1995 | Meade et al. | |
| 5,486,185 A * | 1/1996 | Freitas et al. | 606/142 |
| 5,486,189 A | 1/1996 | Mudry et al. | |
| 5,499,992 A | 3/1996 | Meade et al. | |
| 5,522,830 A | 6/1996 | Aranyi | |
| 5,562,640 A | 10/1996 | McCabe et al. | |
| 5,746,759 A | 5/1998 | Meade et al. | |
| 5,752,951 A | 5/1998 | Yanik | |
| 5,769,841 A | 6/1998 | Odell et al. | |
| 5,782,748 A | 7/1998 | Palmer et al. | |
| 5,817,119 A | 10/1998 | Klieman et al. | |
| 5,868,785 A | 2/1999 | Tal et al. | |
| 5,928,255 A | 7/1999 | Meade et al. | |
| 6,015,426 A | 1/2000 | Griffiths | |
| 6,059,719 A * | 5/2000 | Yamamoto et al. | 600/127 |
| 6,168,605 B1 | 1/2001 | Measamer et al. | |
| 6,273,882 B1 * | 8/2001 | Whittier et al. | 606/1 |
| 6,494,877 B2 * | 12/2002 | Odell et al. | 606/1 |
| 6,733,514 B2 | 5/2004 | Miser | |
| 2003/0050638 A1 | 3/2003 | Yachia et al. | |
| 2003/0065358 A1 | 4/2003 | Frecker et al. | |
| 2003/0069598 A1 | 4/2003 | Miser | |

* cited by examiner

*Primary Examiner* — Michael Peffley
(74) *Attorney, Agent, or Firm* — Brinks Hofer Gilson & Lione

(57) ABSTRACT

A reconfigurable surgical apparatus that includes a surgical instrument assembly that is formed with a hollow manipulation shaft. A linearly or rotationally movable prime mover is received within the shaft and is activated by an actuator located at a proximal end. A coupler is formed about a distal end of the shaft to have a capture ledge that is configured to releasably engage an interchangeable surgical tool that is formed with an anchor adapted to releasably mate to the capture ledge. The coupler may optionally incorporate a frangible portion that severs a portion of the coupler when the interchangeable surgical tool is removed from the apparatus to ensure single use operation of the tool. The apparatus may also have a predetermined mode of failure ensuring a known point of failure upon exposure to a predetermined force. The apparatus may also be partially enclosed by a shroud.

38 Claims, 4 Drawing Sheets

FAILSAFE RECONFIGURABLE SURGICAL APPARATUS

REFERENCE TO RELATED DOCUMENTS

This application is a continuation-in-part of a previous application filed in the United States Patent and Trademark Office on Dec. 19, 2001 entitled "Reconfigurable Surgical Apparatus" and given Ser. No. 10/027,343, now U.S. Pat. No. 7,122,028.

TECHNICAL FIELD

This invention relates to a failsafe reconfigurable surgical apparatus and instrument that includes detachable and interchangeable end tools, which incorporate new end tool connectors and couplers to provide for a predetermined mode of failure.

BACKGROUND OF THE INVENTION

Medical professionals have long recognized the need for surgical instruments that can utilize a multitude of interchangeable tools. What has been needed but heretofore unavailable are surgical instruments that are compatible for use with detachable and interchangeable tools that incorporate universal connectors that establish interchangeability with a multitude of surgical tools and devices. A further need includes tools that incorporate failsafe features that ensure that the instrument fails in a particular way to minimize the risks of patient injury. Such a predetermined failure method ensures that no instrument fragments enter the patient upon failure of the instrument. Yet another shortcoming of the prior art instruments has been their failure to shroud and electrically insulate predetermined portions of the tool, as well as to shield surrounding tissue from inadvertently becoming pinched by the moving elements of the tool.

Such long-felt needs have been particularly prevalent in the field of endoscopic surgical instruments that are used in minimally invasive surgical procedures. These types of procedures are performed through one, two, three, or even four small incisions created in the skin of a patient. In multiple incision procedures, a single endoscopic instrument may be introduced per incision. Each such instrument can be manipulated from the exterior of the patient to remotely conduct a specific surgical operation inside the patient. To lessen the trauma to the patient, it is preferable to minimize the number of such incisions and surgical instruments.

The procedure can involve a relatively non-complex procedure such as a biopsy, as well as complicated cardiothoracic remedial and interventional operations. In the latter, one or more endoscopic tools are needed to perform the procedure and space inside the body of the patient is at a premium. Therefore, any tools that are to be introduced into the surgical field must compete for space with other tools including for example, clamps, cutting tools, fluid injection and suction ports, lighting and visual equipment, and similar devices. Accordingly, those with skill in the art can appreciate that there is limited intracorporeal space available for tools and equipment. Therefore, before one tool can be introduced, another tool may have to be removed. Since only a limited number of minimally invasive type endoscopic surgical instruments are preferably utilized during any given procedure, there has long been a need for the capability to interchange multiple surgical tools on any single endoscopic instrument.

The removability and interchangeability of the tools and reusability of such surgical instrument can reduce costs and complexity. For example, maintenance costs associated with refurbishment, cleaning, and sharpening tools after each surgical procedure is significant. Removable end tools can facilitate such efforts and can also be adapted for single use applications, which eliminates the need for cleaning and refurbishment. During use, tissue and fluids become lodged in the crevices and interstices of small surgical instruments, which complicate sterilization and refurbishment.

Furthermore, the means for connecting the removable tool to the manipulation shaft of the surgical instrument is important to the usefulness of the surgical instrument. The connection must positively secure the components together during operation, and must maintain the connection throughout the range of motion forces typically encountered during surgical procedures. The connection must allow the smooth and controllable transfer of motion from an actuation shaft to the surgical tool. The connection must also facilitate quick and easy connection and disconnection of the interchangeable tool. The connection must be such that it does not become loose and allow movement between the components after repeated use. Further, a connection incorporating a predetermined failsafe mode is desired. The connection should facilitate the transfer of electrical current for certain procedures, while the tool should incorporate electrical insulating properties in those areas necessary to prevent accidental energy transfer to surrounding tissues.

Many attempts have been made to create reconfigurable endoscopic instruments that can employ a variety of surgical tools. One such attempt is a medical instrument that incorporates a handle having scissor grips adapted to actuate a manipulation shaft that is connected to the interchangeable tool, which may be, for example, a grasper, biopsy collector, dissector, or scissor.

Other attempts aimed at reducing maintenance expenses of surgical tools are exemplified by, among other patents, U.S. Pat. No. 4,569,131 to Falk et al. The Falk et al. instrument is a device that has a handle and jaws that are separable from an instrument shaft so that the individual components may be more easily cleaned and sharpened, or disposed of after each use.

Surgical instruments such as that described in U.S. Pat. No. 5,618,303 to Marlowe et al. have attempted to improve joints between components of the instruments. Marlowe et al. discloses a device that includes a stub shaft or link means terminating in an enlarged end that is shaped to be received by a clevis. Other types of joints are described in U.S. Pat. No. 5,304,203 to El-Mallawany et al., which teaches a T-shaped coupling joint.

Likewise, surgeons have long appreciated that complex surgical devices should have built-in failsafe modes so that the patient is not injured if the device should fail. U.S. Pat. No. 5,275,607 to Lo et al. describes such a device directed to intraocular surgery. The '607 device is designed such that if the power fails during surgery the surgeons can manually override the system so that the blades may be closed and the tool removed from the eye. Such a desirable predetermined failsafe mode, preferential mode of failure, or directed point of failure, in some cases, is lacking from the field of reconfigurable surgical instruments.

What continues to be needed but missing from the field of interchangeable surgical tools is a secure connection between components that will not loosen after several uses, which is also designed for improved ease of manufacture and replaceability. While some of the prior art devices attempted to improve the state of the art of interchangeable surgical tools, none has achieved low cost parts that are easy to fabricate and convenient to use. A more desirable interchangeable surgical tool preferably includes a more secure connection, which can be adapted so that different tools can be configured to the surgical instrument. Even more desirable is a tool with a built in predetermined failsafe mode to minimize the chance of patient injury, facilitates selective cauterization, and minimizes the likelihood of damage to surrounding tissue. With these capabilities taken into consideration, the instant invention addresses many of the shortcomings of the prior art and offers significant benefits heretofore unavailable.

SUMMARY OF THE INVENTION

In one embodiment, the present invention is directed to a reconfigurable surgical apparatus, comprising:
  a surgical instrument assembly formed with a hollow manipulation shaft internally receiving a prime mover activated by an actuator located at a proximal end of the shaft;
  a coupler formed about a distal end of the shaft and having a capture ledge; and
  an interchangeable surgical tool attachable to the coupler and including an anchor adapted to cooperate with and mate to the capture ledge; wherein said anchor deforms or has a directed point of failure thereby rendering the apparatus nonfunctional when the anchor is subjected to a predetermined force that is less than the force that causes failure of the prime mover, the actuator, the coupler, or the interchangeable surgical tool.

In its most general sense, the present invention overcomes the shortcomings and limitations of the prior art in any of a number of effective configurations. In one configuration, the reconfigurable surgical apparatus or instrument according to the present invention incorporates, among other elements, a prime mover that is movably positioned within a hollow manipulation shaft. The prime mover is adapted to be activated by an actuator located at a proximal end of the shaft. The shaft also includes a coupler at the distal end which comprises a capture ledge. The surgical apparatus is further configured with an interchangeable surgical tool that is attached to the coupler. The tool also includes a deformable anchor that is adapted to mate to the capture ledge of the coupler.

Thus, there is disclosed a reconfigurable surgical apparatus comprising a surgical instrument assembly formed with a hollow manipulation shaft receiving a prime mover activated by an actuator located at a proximal end of the shaft. The surgical apparatus also includes a coupler formed about a distal end of the shaft with a capture ledge. Further, there is an interchangeable surgical tool which is attachable to the coupler which includes a deformable anchor adapted to mate to the capture ledge.

The coupler is preferably configured to have the capture ledge define a surface or a portion of a surface of at least one lateral aperture or recess, which is sized to receive the anchor. The anchor and the capture ledge are arranged to cooperate during actuation of the prime mover.

In one of many variations of the instant invention, the anchor can be formed as a generally hook shaped tine that is sized and shaped for releasable receipt into the recess and against the capture ledge. The hook shaped tine may also further include an engagement face that is adapted to releasably engage and cooperate with the capture ledge.

Any of the preceding configurations and embodiments may also be adapted with the anchor having a frangible portion. In certain implementations, it may be desired to limit use of the end tool and/or the entire reconfigurable surgical apparatus to a single use. This would ensure the sterility of the apparatus and/or the end tool prior to use.

The frangible portion or directed point of failure may be defined by at least one shear notch. In alternative arrangements, the frangible portion can also be formed to be a weakened material having shear strength that is less than that of the surrounding material. This can be accomplished with either integrally extruded or joined dissimilar materials, or by forming the frangible portion to have a smaller diameter, a scored section, or a notched portion. Such scoring or notches may be a portion of or the entire circumference of a section of the anchor. In embodiments employing frangible portions, the apparatus may be configured so that any small fragments produced by breakage of the frangible portions will be contained within the apparatus until the apparatus may be safely removed from the patient and disassembled.

Thus, there is further disclosed a reconfigurable surgical apparatus comprising a surgical instrument assembly formed with a hollow manipulation shaft receiving a prime mover activated by an actuator located at a proximal end of the shaft. A coupler is formed about a distal end of the shaft having a capture ledge that defines a recess in the coupler. An interchangeable surgical tool adapted to connect to the coupler and formed with an anchor, having a directed point of failure. The anchor adapted to cooperate with and non-releasably mate to the capture ledge and capable of transferring rotational force from the prime mover to the tool.

Also disclosed is a reconfigurable surgical apparatus comprising a surgical instrument assembly with a hollow manipulation shaft receiving a prime mover activated by an actuator located at a proximal end of the shaft. A coupler is formed about a distal end of the shaft having a capture ledge that defines a lateral recess in the coupler. An interchangeable surgical tool for attachment to the coupler and formed with an anchor having a shear notch or other force limiting means for a cirected point of failure.

As described in the various figures, the frangible portion preferably causes a distal section of the anchor to sever or shear apart upon exposure to a predetermined force or disconnect from the coupler. While complete shearing of the distal section is preferable in most configurations, it is not necessary for ensuring that the reconfigurable surgical apparatus is not reused prior to inspection, refurbishment, and replacement of worn or unserviceable components. All that is required in instances where reuse is to be restricted, controlled, or prevented, is that the end tool be prevented from proper coupling to the surgical apparatus. The present invention contemplates many suitable arrangements that are capable of accomplishing such described capabilities. Preventing reuse can be accomplished by incorporating a semi-frangible, distortable, or distendable portion that will deform upon decoupling of the end tool from the distal end of the shaft. In one embodiment, the frangible portion is completely severable and the severed end of the anchor that remains on the tool may be used as a probe that can be inserted into the lateral recess to remove the portion of the severed anchor. The present invention further contemplates that the proximal end of the anchor is adapted to incorporate the coupler. Further, the interchangeable tool is formed with the capture ledge which is adapted to releasably mate to the anchor. This is opposite to the arrangement where the anchor depends from the end tool and the capture ledge and/or the lateral recess is formed in the distal end of the shaft. As in preceding configurations, the lateral recess and the capture ledge can be adapted to releasably receive the anchor.

In a further variation of any of the preceding embodiments, the instant invention is also directed to the reconfigurable surgical apparatus that includes the interchangeable surgical tool being configured to connect to the coupler and having a reciprocating capture member adapted to releasably mate to the anchor. The reciprocating capture member preferably receives the anchor described in previous embodiments and variations and operates to actuate the particular end tool as the anchor-capture member moves in response to linear motion inputs from the actuator.

As with preceding configurations, modifications, and alternatives, the capture member of the instant variation may be formed in the end tool to define at least one lateral recess adapted to cooperate with and releasably receive the anchor. One of many modifications of the anchor includes a generally hook shaped tine having an end sized for cooperation with, and releasable receipt into the recess of the capture member. As before, the hook shaped tine may include an engagement face adapted to releasably engage the capture member.

In yet another configuration, the reconfigurable surgical apparatus according to the present invention includes, among other elements, a surgical instrument assembly having the coupler formed about the distal end of the shaft to include a receiver formed with an engagement ledge and shelf. The assembly also incorporates an interchangeable surgical end tool that is attached to the coupler, and which includes an engager that is adapted to releasably mate to the receiver.

The preferred receiver according to the invention includes a generally hook shaped recess that is adapted to cooperate with and releasably mate with the engager. Further, the engager is formed with a generally hook shaped tine that is formed to releasably mate with the receiver. Thus, there is disclosed a reconfigurable surgical tool comprising a surgical instrument assembly formed with a hollow manipulation shaft receiving a prime mover activated by an actuator located at a proximal end of the shaft. A coupler formed about the distal end of the shaft includes a receiver having a capture ledge and an interchangeable surgical tool attachable to the coupler and including an anchor adapted to cooperate with and mate to the capture ledge.

A further variation of the engager-receiver configuration can incorporate a frangible or deformable portion that is similar in operation to any of the preceding arrangements. More specifically, the frangible portion may be configured to, among other features and capabilities, limit the interchangeable surgical end tool to a single use so as to afford an opportunity for a post-use safety and serviceability inspection and for refurbishment and replacement of components or the entire end tool. Additionally, the frangible portion may incorporate any of the previously described features, elements, and capabilities, and may be defined as one or more shear notches, which notches may be confined to a small region of the exterior circumference of the shaft of the engager, the receiver, or both. Also, the one or more notches may be circumferentially formed so as to establish one or more regions of the engager-receiver coupler that is/are of a generally reduced diameter relative to the non-notched portion thereof.

Thus, there is further disclosed a reconfigurable surgical tool comprising a surgical instrument assembly formed with a hollow manipulation shaft internally receiving a prime mover activated by an actuator located at a proximal end of the shaft; a coupler formed about a distal end of the shaft and incorporating an anchor; and an interchangeable surgical tool adapted to cooperate with and connect to the coupler and formed with a capture ledge adapted to cooperate with and mate to the anchor and capable of transferring rotational force from the prime mover to the tool wherein the anchor is sealed from an exterior environment by the coupler and the manipulation shaft.

Preferably, the frangible portion establishes a region of the engager-receiver coupler that is weakened relative to the surrounding structure. Even more preferably, the comparatively weakened region serves as a fracture zone that severs the engager from the surgical end tool or from the shaft in alternative arrangements, when the surgical tool is decoupled from the surgical instrument assembly. As with prior embodiments, variations, and modifications, the severed end portion of the engager that remains can be used to remove the portion of the anchor that may remain engaged with the capture ledge and in the lateral recess.

In yet other alternatives to any of the above-described configurations, the engager and receiver may be formed in alternate positions whereby the engager depends from the distal end of the prime mover, and the receiver is incorporated into the surgical tool. Additionally, the receiver, in any of the preceding embodiments, may further define a generally hook shaped recess that can be adapted in cooperation with the engager to releasably receive the engager. The engager may also be formed with a generally hook shaped tine that is sized and configured to be releasably received in the recess, in cooperation with the receiver, to effect the releasable mating to the receiver.

Additional embodiments incorporate failsafe features into the apparatus. A failsafe mode is incorporated into the apparatus by selecting a particular element, and location on that element, to be weaker than the other portions of the apparatus. Therefore, if a user attempts to exert too much force with the apparatus it will fail in a known location at a predetermined level of force. Incorporating such a failure point internal to the apparatus allows a surgeon to confidently remove a failed apparatus from a patient knowing that no shards of instrument remain in the patient. By way of example and not limitation, in an embodiment including a surgical scissors, the deformable or frangible parts may be constructed to fail at a lower force than would be required to chip or break the blades of the scissors. Therefore, should an unexpectedly hard object be encountered by the instrument, or should the operator apply excessive force to the instrument, the failsafe features will render the instrument non-operable before a force level that might chip or break the scissor blades is achieved.

Incorporation of such a failsafe mode may be accomplished through the use of an anchor that deforms when subjected to a predetermined force such that the anchor can no longer mate with its cooperating portion of the apparatus thereby rendering it nonfunctional. Alternatively, the failsafe mode may be incorporated into the frangible portion. Regardless, the predetermined force that renders the apparatus nonfunctional is one that is less than the force required to cause failure in the other components of the apparatus. Therefore, when that apparatus is subjected to a force that places any portion of the apparatus at risk of failure, the anchor predictably fails before the other components thereby virtually eliminating any risk to the patient.

These variations, modifications, alternatives, and alterations of the various preferred embodiments, arrangements, and configurations may be used alone or in combination with one another as will become more readily apparent to those with skill in the art with reference to the following detailed description of the preferred embodiments and the accompanying figures and drawings.

BRIEF DESCRIPTION OF THE DRAWINGS

Without limiting the scope of the present invention as claimed below and referring now to the drawings and figures, wherein like reference numerals and numerals with primes and double primes across the several drawings, figures, and views refer to identical, corresponding, or equivalent elements, features, and parts:

DESCRIPTION OF THE PREFERRED EMBODIMENTS

The apparatus of the instant invention provides a significant advance in the state of the art of interchangeable surgical tools. The preferred embodiments of the reconfigurable end surgical tool accomplish this by new and novel arrangements of elements that are configured in unique and novel ways and which demonstrate previously unavailable but preferred and desirable capabilities.

The detailed description set forth below in connection with the drawings is intended merely as a description of the presently preferred embodiments of the invention, and is not intended to represent the only form in which the present invention may be constructed or utilized. The description sets forth the designs, functions, means, and methods of implementing the invention in connection with the illustrated embodiments. It is to be understood, however, that the same or equivalent functions and features may be accomplished by different embodiments that are also intended to be encompassed within the spirit and scope of the invention as set forth in the claims.

Figure 1:
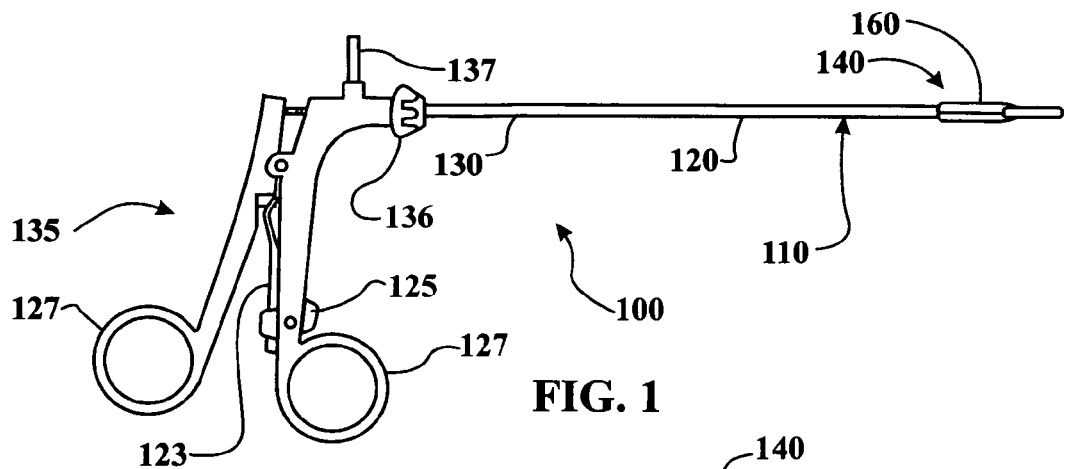
FIG. 1 is an elevation view, in reduced scale, of a reconfigurable surgical apparatus according to the present invention.
Figure 2:
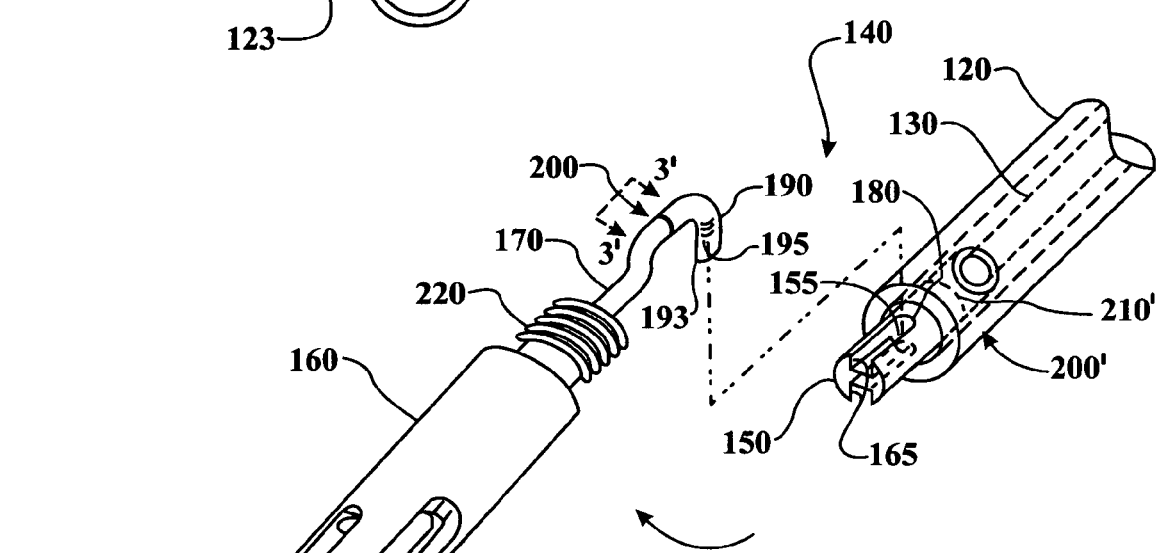
FIG. 2 is a detail perspective exploded view, in enlarged scale and rotated, of the distal end of the reconfigurable surgical apparatus shown in FIG. 1.
Figure 3:
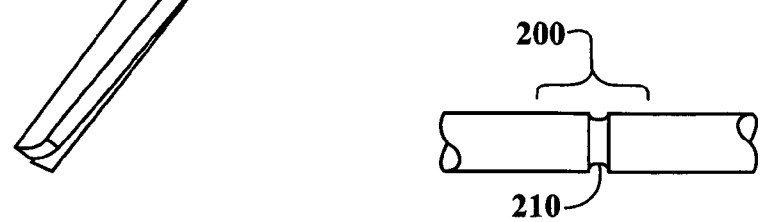
FIG. 3 is a side view, in enlarged scale and rotated, taken along view line 3'-3' of FIG. 2.
Figure 4:
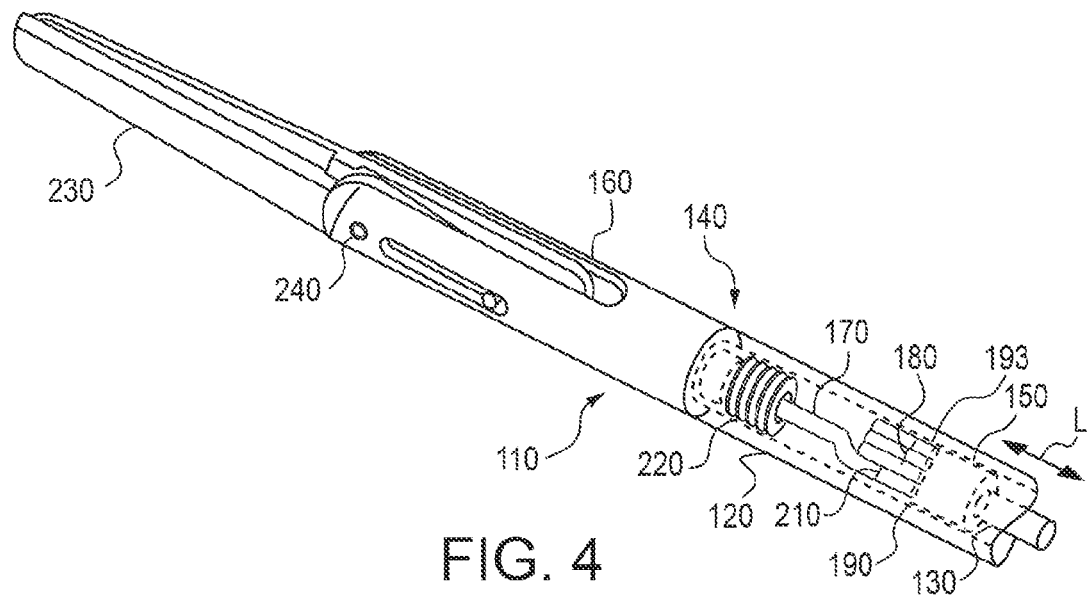
FIG. 4 is a perspective view of the assembled reconfigurable surgical apparatus shown in FIG. 2.

With reference generally now to FIGS. 1 through 6, and more specifically to FIGS. 1, 2, and 4, in one of the many preferable arrangements, the reconfigurable surgical apparatus 100 according to the present invention includes, among other elements, a surgical instrument assembly 110. The assembly 110 also includes a prime mover 130 that can be positioned within a hollow manipulation shaft 120 and which is adapted to impart a range of motion. The prime mover 130 is activated by an actuator 135 located at a proximal end of the shaft 120, which is configured to remotely impart the desired range of motion. Various types of manually, remotely, mechanically, and automated actuators are known to those with skill in the art. As described generally in the various figures and as shown in FIG. 1 for purposes of an exemplar, a manual scissors handle-type actuator 135 can be employed for purposes of the present invention. Although the hollow manipulation shaft 120 is shown with a single lumen, it can be formed with multiple lumens that can be adapted for receipt of various other elements in addition to the prime mover 130. Additionally, the entire reconfigurable surgical apparatus 100 can be sized and configured for receipt within a larger minimally invasive surgical instrument that is introduced intracorporeally and which is adapted to receive the surgical apparatus 100 contemplated herein.

In exemplary configurations, the actuator 135 is adapted to cooperate with a rigging cord 123 that is adjusted with a release latch 125. The cord 123 is preferably linked or directly connected to the actuator 135 and is adjusted to control the range of motion of the prime mover when the handles 127 of the actuator 135 are operated. In variations of the present invention, the actuator 135 may also incorporate one or more ports 137 that can be adapted to receive additional elements such as fluid lumens and additional prime movers that can be configured to add further functionality and more complex motion to the instrument assembly 110. For example, a directional guide wire (not shown but known to those having skill in the art) can be received through the port 137. Such a guide wire is useful and can facilitate intracorporeal introduction of the surgical instrument assembly 110 during minimally invasive surgical procedures that require insertion of the instrument 110 through cutaneous incisions and ports in the body of a patient. The prime mover 130 is shown in the figures as configured for linear motion, however, the mover 130 can be augmented and or replaced with a similar element (not shown but within the skill in the art) that can be configured for rotational motion. Also, those having ordinary skill in the art can understand that either of such elements, the prime mover 130 or such other elements, can be configured for both linear and rotational motion in certain arrangements of the surgical instrument 110. Rotational motion can be facilitated through incorporation of a finger wheel 136 on the manipulation shaft 120.

With continued reference to the various figures and specifically now also to FIG. 2, the surgical instrument assembly 110 also further incorporates a coupler 140 that is formed about a distal end of the prime mover 130. In one of various arrangements, the coupler 140 incorporates a capture member 150 that is formed with a capture ledge 155. The surgical instrument assembly 110 is compatible for use with and includes any of a wide number of end effectors that are selected according to the surgical intervention to be accomplished. For example, such end effectors can include application specific interventional tools, such as scalpels, dissectors, biopsy collectors, drills, tweezers, scissors, catheters, lumens, stents, balloons, as well as active and passive observational probe, visual, and illumination devices, and combinations thereof. For purposes of illustration but not limitation, the instrument assembly 110 of the various figures is shown to include an interchangeable surgical tool 160 in the general form of scissors. The coupler 140 also includes one or more cooperating elements on the interchangeable surgical tool 160, which are adapted to connect the tool 160 to the coupler or coupling mechanism 140 portion that depends from the distal end of the prime mover 130. In this configuration, the coupler 140 incorporates an anchor 170 that is adapted to releasably mate with the capture ledge 155.

In the exemplary arrangement of the instant invention shown in FIG. 2, the coupler 140 portion of the interchangeable surgical tool 160 is preferably formed to define at least one lateral aperture or recess 180 that includes at least one surface that can be the capture ledge 155. The capture ledge 155 and the recess 180 can be formed and arranged to releasably receive and retain the anchor 170. Any of a large number possible anchor configurations may be suitable for purposes of the present invention, and can include, for purposes of illustration but not limitation, the anchor 170 formed as a generally hook shaped tine 190 that has an end 193, which tine 190 and end 193 are preferably sized for releasable receipt into the recess 180. The hook shaped tine 190 may also further include an engagement face 195 that is adapted to releasably or non-releasably engage the capture ledge 155.

Although generally featureless surfaces are shown about the ledge 155, on the engagement face 195, and in the recess 180 in the various figures, the present invention contemplates further modifications to the ledge 155, the face 195, and the recess 180 wherein the respective surfaces can be modified for additional functionality and interoperability. For example without limitation, the engagement face 195 and the ledge 155 may be modified to incorporate cooperating and/or locking features, such as gear teeth and notches that operate to mesh together upon receipt of the anchor 170 in the recess 180. Other alternative configurations may include surface textures adapted to create further enhancements to the interface between the recess 190, the engagement face 195, and the capture ledge 155. One such variation can include a unidirectional tooth and pawl ratchet mechanism wherein ramp or tooth-type structures are formed on the engagement face 195 and one or more pawl-type structures are formed on or about the hook shaped tine 190.

Examples of such locking features that are known in the art include, for example without limitation, wire and cable tie devices such as those disclosed in U.S. Pat. Nos. 4,214,349 and 4,135,749, which are collectively incorporated herein by reference in their entirety. Incorporation of such features into the device according to the present invention can be desirable for applications wherein the interchangeable surgical tool 160 is to be used one time only or where the tool must be inspected and refurbished between uses to ensure safety and operability. With such ratcheting features, the tine 190 of anchor 170 can be snapped, threaded, or inserted into the recess 180 in one direction, but cannot be removed therefrom in the retrograde direction. In this preferred variation, the tine 190 can be removed from the recess 180 only after being severed from the anchor 170 and then by being pushed out of the recess 180 in the required direction.

Any of the preceding and later described embodiments of the apparatus 100 may also optionally incorporate one or more orientation and alignment recesses or keyways 165 that may be formed in any of the components and elements of the instant invention and which are operative to facilitate alignment of the capture member 150 and the anchor 170 of the coupler 140. As reflected in FIGS. 2 and 4, two generally longitudinal keyways are formed in the capture member 150 and are adapted to nestingly receive a segment of the installed anchor 170.

Prior to operation and use of the reconfigurable surgical apparatus 100 according to the instant invention, the anchor 170 is engaged with the capture ledge 155 wherein the hook shaped tine 190 is received in the recess 180. Next, the capture member 150 is retracted into the hollow manipulation shaft 120, and the interchangeable surgical tool 160 is secured to the shaft 120 with the connector 220. The connector 220 may take the form of any of a number of connection devices including, for example without limitation, threads, twist and lock type elements that operate with partial relative rotation much like the so-called child-proof medicine bottle caps and automotive gas tank filler port caps, pin and clevis connectors, clamp and post type frictional connectors, chuck and pin type devices that operate in a manner similar to that of drill bits and chucks, key and keyway and cotter couplers, bayonet type connectors similar to those used in camera lens mounts and in some computer related network cabling components, and scarf joint type couplers. In one of many variations, the connector 220 may take the form of a threaded connection, as shown for purposes of illustration in FIGS. 2, and 4 through 6. In this variation, the male connector threads 220 are receivably engaged with cooperating female threads formed within the coupler 140 at the distal end of the manipulation shaft 120.

With continued reference to the various figures and illustrations, and with specific reference now also to FIGS. 2, 3, and 4, those with skill in the art can observe that the reconfigurable surgical apparatus 100 is assembled and nearly ready for use once the connector 220 is engaged and the coupler 140 joins the interchangeable surgical end effector or tool 160 to the surgical instrument assembly 110. After the coupler 140 is secured, the user typically rigs the apparatus 100 for operation by, as noted generally hereinabove, by releasing the adjustment cord release latch 125 and adjusting the actuator cord 123 so as to establish the desired range of linear motion, as opposed to rotational motion that may be imparted with a finger wheel 136. For continued purposes of illustration, the described linear motion of the prime mover 130 is shown generally by the arrows of FIG. 4 that are identified by reference letter "L". In this arrangement, the linear motion of the prime mover 130 can, during operation of the actuator 135, be transferred through the capture member 150, to the hook shaped tine 190 of the anchor 170, to in turn actuate the interchangeable surgical tool 160.

In a further embodiment, the anchor 170 may be formed to incorporate a predetermined failsafe mode. For example, the anchor 170 may be designed to deform such that the anchor 170 can no longer cooperate and mate with the capture ledge 155 thereby rendering the apparatus 100 nonfunctional. The ideal point at which the anchor 170 deforms rendering the apparatus 100 nonfunctional can be precisely determined and accurately implemented by an engineer with skill in the art. Generally, deformation is selected to occur when the anchor 170 is subjected to a predetermined force that is less than the force that causes failure in other components of the apparatus, thus ensuring a known mode of failure. In embodiments such as that shown in FIG. 2, a level of predetermined force necessary to deform the anchor 170 is less than about 90, more preferably greater than 50 pounds of force, and most preferably about 70 pounds of force.

Each physician hand differs in size, shape and musculature and the amount of force that the physician can apply to the actuator 135 varies greatly. Device manufacturers design instruments with large mechanical advantages (up to 20:1) in order to assist the weakest hand so as to perform the intended task efficiently and effortlessly. Device manufacturers also design instruments with a built in safety factor to accommodate the extremely strong hand. Frequent use of excessive force on instruments leads to material fatigue and even fracturing of the components. Loss of these small parts in the operating arena can lead to extensive patient injury and increased recovery time.

Since these instruments for minimally invasive surgery are miniaturized, these instruments are more sensitive to force exerted on them and the individual components have limited ability to absorb excessive forces. Device manufacturers often warn clinicians of the potential dangers of misuse and excessive force, however, the practitioner has no way of knowing how much force is excessive with the prior art devices. The present invention with its failsafe and/or foolproof anchor with an engineered breaking point solves this long felt need.

Figure 7:
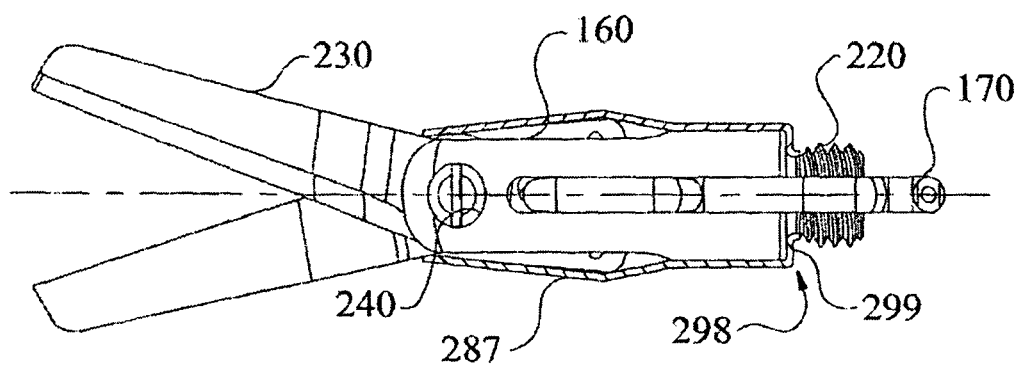
FIG. 7 is a partial cross-sectional view of a surgical tool according to the invention wherein the sheath made of heat shrinkable tubing is in cross section.

One with skill in the art will appreciate the benefits associated with a known mode of failure. In the field of surgical instruments, having a predetermined known mode of failure such as that of the anchor 170 of FIG. 2 ensure that in the event that failure occurs the surgeon can remove the instrument knowing that no portions of the instrument are left in the patient. In one specific embodiment of the invention, the proximal end of the tool 160 is covered in a shroud of heat shrinkable tubing 287. As seen in FIG. 7, the shroud of heat shrinkable tubing 287 covers the tool 160 from about the pivot pin 240 to the proximal end of the tool at 299. Heat shrinkable tubing is well known to those in the medical device art and essentially completes the enclosure of the tool 160 to prevent any parts from entering the operating field should the anchor 170 fail, break or bend in any way.

Figure 8:
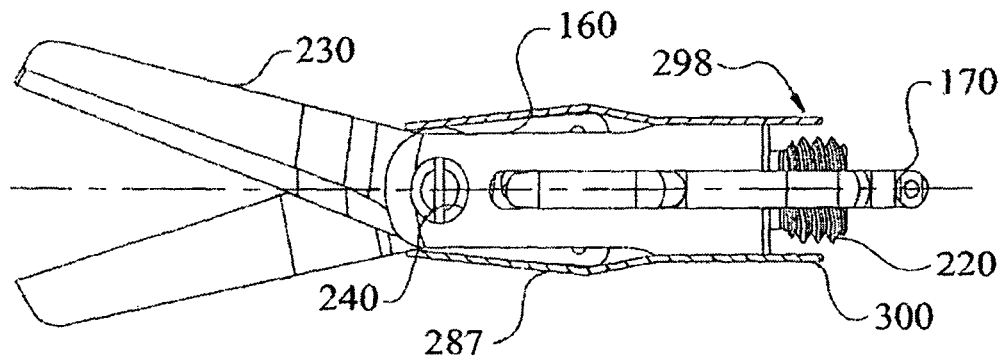
FIG. 8 is a partial cross-sectional view of one embodiment of the present invention wherein the sheath of heat shrinkable tubing is in cross section and comprises a skirt.

FIG. 8 shows yet another embodiment wherein the heat shrinkable tubing 287 extends in a skirt-like manner beyond the proximal end 299 of the tool 160. The skirt 300 will then engage the distal end of the hollow shaft 120, thereby ensuring smooth and efficient operation of the instrument. The heat shrinkable tubing 287 or shroud also seals the distal end of the anchor from the exterior environment.

An additional benefit associated with this embodiment is that different surgical tools 160, such as scalpels, dissectors, biopsy collectors, tweezers, scissors, etc., may have different predetermined forces that render the apparatus 100 nonfunctional. This ensures that no more force that is absolutely necessary for a particular procedure is exerted on the organs of a patient. A predetermined failsafe mode may not only be accomplished via deformation of the anchor, but also breakage of the anchor, as discussed below. By way of example and not limitation, in an embodiment including a surgical scissors, the deformable or frangible parts may be constructed to fail at a lower force than would be required to chip or break the blades of the scissors. Therefore, should an unexpectedly hard object be encountered by the instrument, or should the operator apply excessive force to the instrument, the failsafe features will render the instrument non-operable before a force level is achieved that might chip or break the scissor blades.

With specific reference also now to FIG. 3, a further variation of the reconfigurable surgical apparatus 100 includes a frangible portion 200, which in the various figures is reflected to be in the anchor 170. The frangible portion 200 can be incorporated to limit the interchangeable surgical tool 160 to a single use, which may be beneficial in a number of circumstances. Most commonly, in recognition of the wear and deterioration that can result from normal use of the surgical tool 160, it may be desirable that the tool 160 be limited to single use applications. This requirement and need is especially pronounced in circumstances where the surgical tool 160 may be constructed of less expensive, recyclable, lightweight, or hybrid materials that are more susceptible to failure after repeated use. Some high-strength and durable materials can experience significant wear even after only a single use. This has been demonstrated in a variety of routine surgical interventions including, for illustration purposes without limitation, procedures performed on bone and that may require the location and removal of foreign bodies such as chipped bone fragments, calcified deposits, and other undesirable objects.

Any of the preceding embodiments, configurations, and variations of the present invention may be modified to incorporate the frangible portion 200, which may be constructed in any of a number of ways, and in any number of locations about the reconfigurable surgical apparatus 100. Preferably, the frangible portion 200 is formed on either the surgical instrument assembly 110 or the interchangeable surgical tool 160, or both, proximate to the coupler 140. More preferably, the frangible portion 200 is formed about either the anchor 170 or the capture member 150.

For purposes of continued illustration, the frangible portion 200 reflected in the various figures, including FIGS. 2 and 3 is shown to be formed as a circumferential region of reduced diameter, or a generally toroidal, parabolic, or counter-sink shaped shear-type notch 210 that is formed about a portion of the anchor 170. A similar frangible portion (not shown) can be implemented wherein the frangible portion 200 may be replaced or augmented with a region that is formed by a material of construction of the anchor 170 that is weaker than the surrounding material of the anchor 170. This can be accomplished with either a non-circumferential notch, a diametrical or lateral notch formed in the anchor 170, or functional equivalents thereof. In yet additional examples, the frangible portion 200 may also be formed wherein the material of the anchor 170 material is selected to have a material strength that is reduced in the region of the frangible portion 200 relative to the other portions of the anchor 170. Another variation may include forming a circumferential score about the anchor 170 in the region of the frangible portion 200. An additional method includes forming at least one non-circumferential shear notch, which may be similar in cross-section to the notch 210, within the frangible portion 200 by removing material from the anchor 170 by machining, or by molding the anchor 170 to have the illustrated shear notch 210 or some similar feature.

Not only can the frangible portion 200 be used to ensure a single use of the apparatus 100, but it may be used in the creation of a predetermined failsafe mode. For instance, the predetermined mode of failure may be instigated by breakage of the anchor 170 at the frangible portion 200, rather than by deformation of the anchor 170 as previously disclosed. Therefore, as one with skill in the art will appreciate, the frangible portion 200 may serve the dual purpose of ensuring the single use of an instrument as well as providing for a predetermined mode of failure. Additionally, the location of the frangible portion 200, or the predetermined location of failure, may be selected to ensure that upon failure no portions of the nonfunctional apparatus 100 enter the patient. The point at which the frangible portion 200 breaks rendering the apparatus 100 nonfunctional can be precisely determined and accurately implemented. Generally, deformation is selected to occur when the anchor 170 is subjected to a predetermined force that is less than the force that causes failure in the other components of the apparatus ensuring a known mode of failure. In embodiments employing frangible portions, the apparatus may be configured so that any small fragments produced by breakage of the frangible portions will be contained within the apparatus until the apparatus may be safely removed from the patient and disassembled.

Those with skill in the art can appreciate that the frangible portion 200, or shear notch 210, according to the preferred examples, may be incorporated in any number of locations along the anchor 170, or other components and elements of the apparatus 100. FIGS. 2 and 4 illustrate only one such position, from among many possible locations of the apparatus 100, along the portion of the anchor 170 that is located proximate to the capture ledge 155, when the coupler 140 is in the assembled configuration. Another alternative or additional location of the frangible portion 200, or shear notch 210, is on a segment of the hook shaped tine 190. The tine location facilitates the embodiment previously described in which the hook shaped tine 190 cannot be removed from the recess 180 unless the tine 190 is sheared from the anchor 170. This variation leaves the straight portion of the tine 190 in the recess 180, where it can be forced out of the recess 180 by using the severed end of the anchor 170 that remains on and depends from the tool 160 after severing. In operation, during decoupling of the tool 160 from the instrument assembly 110, the frangible portion 200 of the anchor 170 is severed. The apparatus 100 may be configured whereby the severing operation occurs immediately upon decoupling the coupler 140 by unthreading the connector 220. Alternatively, the severing operation can be performed manually after the tool 160 is disconnected from the distal end of the shaft 120. As described above, the portion of the anchor 170 that remains on the tool 160 may then be used to remove the portion of the anchor 170 remaining in the capture ledge 155 from the lateral recess 180 by pushing the severed end into the recess to dislodge the severed segment of the tine 190. Referring again to FIG. 2, a further optional variation of the capture member 150 includes a frangible portion 200' that is formed in the capture member 150. The frangible portion 200' may be formed by any of the previously detailed means.

As already described, many various types of interchangeable surgical tools 160 are contemplated for use with the present invention. As reflected in the various figures for purposes of illustration, a tool 160 is shown that is compatible for use with reciprocating linear motion during operation. More specifically, the various figures depict the tool 160 to be an endoscopic scissors tool having blades 230 adapted to move about pivot pin 240 during actuation.

Figure 5:
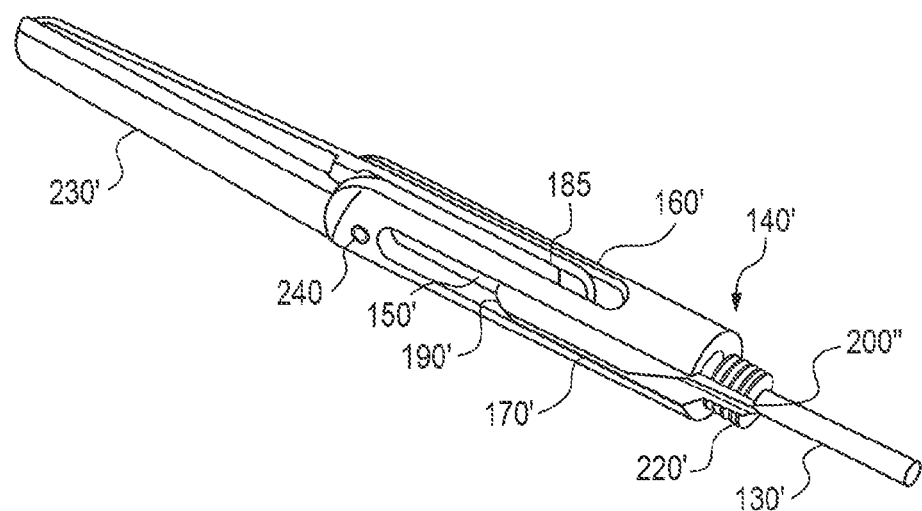
FIG. 5 is a perspective view, in enlarged scale, of a modification of the reconfigurable surgical apparatus shown in FIG. 1, with some structure removed for clarity.

With reference now also to FIG. 5, any of the preceding embodiments may be further modified to incorporate a modified prime mover 130' that includes an anchor 170' adapted for compatibility with an interchangeable surgical tool 160' that receives the anchor 170' in an integrally formed capture member 150', which may or may not also include any other connecting structure. Further alterations to this variation may also incorporate a frangible portion 200' that may be formed in any element of the coupler 140', such as, for example, on the prime mover 130'. In FIG. 5, reference numerals with primes denote structural elements similar or identical to analogous components in the other figures that are identified by reference numerals without any prime or with double primes.

Figure 6:
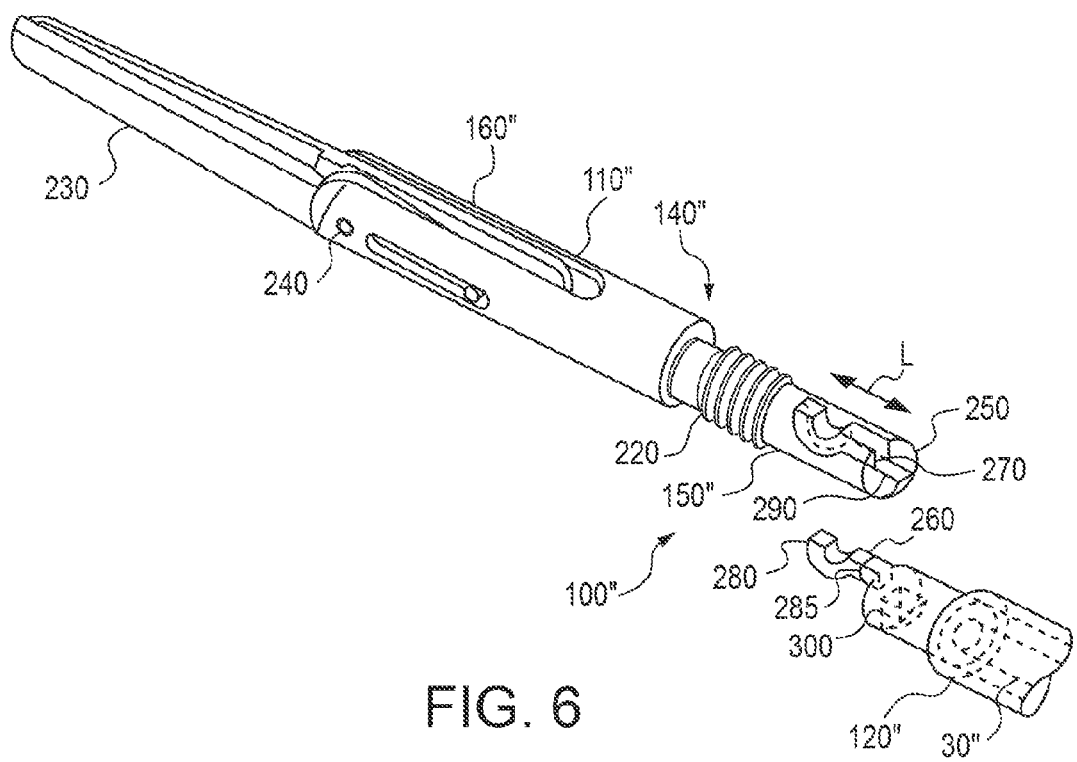
FIG. 6 is an elevated perspective view, in enlarged scale, of a variation of the reconfigurable surgical apparatus shown in FIG. 1.

The instant invention is also further directed to embodiments that include a reconfigurable surgical apparatus 100, such as that shown in FIG. 6, which includes many of the preceding features, elements, components, and capabilities. In FIG. 6, the apparatus 100" also further includes a coupler 140" that has a receiver 250 formed in an interchangeable surgical tool 160". The receiver 250 is adapted to releasably capture an engager 260 that is formed in a distal end of the prime mover 130". The receiver 250 defines a recess 270 that is shaped to receive and capture, in cooperation with the engager 260, an interlocking tine 280 that forms an outwardly projecting portion of the engager 260.

The exemplary configuration of the apparatus 100 shown in FIG. 6 may also further incorporate an engagement shelf 290 projecting from the receiver 250 and an alignment recess 300 adapted to receive and capture the engagement shelf 290. As with previous embodiments, the instant configuration may also further include a frangible portion 285 that may be formed in any of the components, and which is reflected in FIG. 6 as a scored region formed in the interlocking tine 280. Any of the previously described locking features and elements may be formed on the tine 280 and the receiver 250 to establish a "snap" together connection that can be forced apart only by severing the frangible portion 285.

Further embodiments of the tool 160 may incorporate a shroud 287 of heat shrinkable tubing covering a portion of the tool 160, as seen in FIG. 7 and FIG. 8. The shroud 287 of heat shrinkable tubing is formed to fit tightly over the tool 160. The shroud 287 may be formed in a number of ways. For instance, the shroud of FIG. 7 incorporates a feature whereby the shroud 287 wraps around the end 299 of the tool 160 and seals near the connector 220. In an alternative embodiment, the shroud 298 of FIG. 8 is a skirt 300 that extends from the proximal end 299 of the tool 160 to create a seal with the shaft 120 when the apparatus is assembled. This seal created between the hollow manipulator shaft 120 and the tool 160 minimizes the likelihood of debris entering the shaft 120 or the tool 160 and further ensures that there are no exposed metallic edges at the joint that may cause inadvertent energy transfer such as cauterizating.

The shroud 287 may be constructed of any number of materials but is preferably constructed of an electrically insulating material. When the shrouds 287 of FIGS. 7 and 8 are constructed of electrically insulating material, then only the exposed blades may transfer current and cauterize tissue. Such embodiments prevent inadvertent cauterizing of tissue surrounding the tool 160. Additionally, the material of the shroud 287 may incorporate heat shrinking features so that a blank sleeve may be inserted over the desired portion of the tool 160 and then heated to shrink the shroud 287 over the tool 160.

Generally, it is desirable to locate the shroud 287 over any moving parts of the tool 160 that are not directly involved in the function of the tool 160. In this fashion, the shroud 287 prevents tissue surrounding the tool 160 from becoming pinched and potentially damaged by contact with certain moving parts of the tool 160. Additionally, by covering such moving parts, the likelihood that a bone fragment or other impediment becoming lodged in the tool, thereby rendering it nonfunctional, is minimized.

INDUSTRIAL APPLICABILITY

The present invention provides the medical community with a surgical instrument that prevents the re-use of the operative portion through the incorporation of a frangible portion and incorporates a predetermined mode of failure. This provides insurance that surgical procedures will be started with the sharpest and most sterile surgical instruments and that upon failure of an instrument no loose fragments of the instrument remain in the patient.

Numerous alterations, modifications, and variations of the preferred embodiments disclosed herein will be apparent to those skilled in the art and they are all anticipated and contemplated to be within the spirit and scope of the instant invention. For example, although specific embodiments have been described in detail, those with skill in the art will understand that the preceding embodiments and variations can be modified to incorporate various types of substitute and or additional or alternative materials, relative arrangement of elements, and dimensional configurations for compatibility with the myriad possible surgical interventions and endoscopic procedures. Accordingly, even though only few variations of the present invention are described herein, it is to be understood that the practice of such additional modifications and variations and the equivalents thereof, are within the spirit and scope of the invention as defined in the following claims.

We claim:

1. A reconfigurable surgical apparatus, comprising:
    a surgical instrument assembly formed with a hollow manipulation shaft internally receiving a prime mover activated by an actuator located at a proximal end of the shaft, wherein the prime mover comprises a capture ledge and an interchangeable surgical tool comprising
  an outer connector attachable to the hollow manipulation shaft and
  an inner connector attachable to the prime mover and including an anchor adapted to cooperate with and mate to the capture ledge of the prime mover; and
wherein, when the anchor is subjected to a predetermined force that is less than the force that causes failure of the prime mover, the actuator, the outer connector, or the interchangeable surgical tool, said anchor deforms, thereby rendering the apparatus nonfunctional.

2. The apparatus according to claim 1, wherein the proximal end of the interchangeable surgical tool is sealed from an exterior environment by a shroud.

3. The apparatus according to claim 1, wherein the predetermined force applied to the prime mover is less than 90 pounds of force.

4. The apparatus according to claim 1, wherein the anchor is formed with at least one generally hook shaped tine, a frangible portion, and an engagement face adapted to cooperate with and engage the capture ledge.

5. The apparatus according to claim 4, wherein the frangible portion is designed to break in an orientation substantially orthogonal to a direction of translation of the prime mover.

6. The apparatus according to claim 1, further including a shroud configured to cover at least a portion of the interchangeable surgical tool.

7. The apparatus according to claim 6, wherein the shroud is formed to include a shroud end closure to substantially seal the joint between the hollow manipulation shaft and the tool.

8. The apparatus according to claim 7, wherein the shroud end closure is a connector closure formed such that the shroud wraps around the proximal end of the tool and terminates near the connector.

9. The apparatus according to claim 6, wherein the shroud end closure is a shaft closure formed such that the shroud extends from the tool toward the shaft such that when the connector and the shaft are engaged, the shaft closure covers at least a portion of the hollow manipulation shaft.

10. A reconfigurable surgical apparatus, comprising:
  a surgical instrument assembly formed with a hollow manipulation shaft internally receiving a prime mover activated by an actuator located at a proximal end of the shaft;
  the prime mover comprising a capture ledge that defines a lateral recess; and
  an interchangeable surgical tool comprising an outer connector attachable to the hollow manipulation shaft and an inner connector;
  the interchangeable surgical tool attachable to the prime mover, the inner connector of the interchangeable surgical tool being formed with an anchor having a directed point of failure, wherein the anchor is adapted to cooperate with and mate to the capture ledge and is capable of transferring rotational force from the prime mover to the tool.

11. The apparatus according to claim 10, wherein the directed point of failure is designed to break when subjected to a predetermined force that is less than the force that causes failure of the prime mover, the actuator, the capture ledge, or the interchangeable surgical tool.

12. The apparatus according to claim 10, wherein the anchor is sealed from an exterior environment by a region of the interchangeable tool and the manipulation shaft.

13. The apparatus according to claim 10, further including a shroud configured to cover at least a portion of the interchangeable surgical tool.

14. The apparatus according to claim 13, wherein the shroud is formed to include a shroud end closure to substantially seal the joint between the hollow manipulation shaft and the tool.

15. The apparatus according to claim 14, wherein the shroud wraps around the proximal end of the tool and terminates near the connector.

16. The apparatus according to claim 13, wherein the shroud extends from the tool toward the shaft such that when the connector and the shaft are engaged the shroud covers at least a portion of the hollow manipulation shaft.

17. The apparatus according to claim 10, wherein the anchor is sealed from an exterior environment by a shroud.

18. A reconfigurable surgical apparatus, comprising:
  a surgical instrument assembly formed with a hollow manipulation shaft internally receiving a prime mover activated by an actuator located at a proximal end of the shaft;
  the prime mover incorporating an anchor; and
  an interchangeable surgical tool comprising an outer connector attachable to the hollow manipulation shaft and an inner connector;
  the interchangeable surgical tool adapted to cooperate with and connect to the prime mover and formed with a capture ledge adapted to cooperate with and mate to the anchor and capable of transferring rotational force from the prime mover to the tool wherein the anchor is sealed from an exterior environment by the manipulation shaft, and wherein said anchor comprises a directed point of failure.

19. The apparatus according to claim 18, wherein the anchor deforms such that the anchor can no longer cooperate and mate with the capture ledge thereby rendering the apparatus nonfunctional when the anchor is subjected to a predetermined force that is less than the force that causes failure of the prime mover, the actuator, or the interchangeable surgical tool.

20. The apparatus according to claim 19, wherein the predetermined force is less than 90 pounds of force.

21. A reconfigurable surgical apparatus, comprising:
  a surgical instrument assembly formed with a hollow manipulation shaft internally receiving a prime mover activated by an actuator located at a proximal end of the shaft;
  the prime mover comprising a generally hook shaped anchor having an engagement face; and
  an interchangeable surgical tool comprising an outer connector attachable to the hollow manipulation shaft and an inner connector attachable to the prime mover;
  the interchangeable surgical tool formed at an end with a capture ledge that defines a lateral recess in the tool, the ledge being adapted to cooperate with and mate to the engagement face of the anchor and capable of transferring rotational force from the prime mover to the tool.

22. The apparatus according to claim 21, wherein the anchor is sealed from an exterior environment by at least the manipulation shaft, and being configured such that, when the anchor is subjected to a predetermined force that is less than the force that causes failure of the prime mover, the actuator, the capture ledge, or the interchangeable surgical tool, the anchor deforms such that the anchor can no longer cooperate and mate with the capture ledge thereby rendering the apparatus nonfunctional.

23. The apparatus according to claim 22, wherein the predetermined force is less than 90 pounds of force.

24. The apparatus according to claim 23, further comprising a shroud configured to cover at least a portion of the interchangeable surgical tool.

25. The apparatus according to claim 24, wherein the shroud is formed to seal the joint between the hollow manipulation shaft and the tool.

26. The apparatus according to claim 25, wherein the shroud end closure is formed such that the shroud wraps around the proximal end of the tool and terminates near the connector.

27. The apparatus according to claim 24, wherein the shroud extends from the tool toward the shaft such that when the connector and the shaft are engaged the shroud covers at least a portion of the hollow manipulation shaft.

28. A reconfigurable surgical tool, comprising:
a surgical instrument assembly formed with a hollow manipulation shaft internally receiving a prime mover activated by an actuator located at a proximal end of the shaft;
the prime mover including a receiver having an engagement ledge and shelf;
an interchangeable surgical tool comprising an outer connector attachable to the hollow manipulation shaft and an inner connector that includes an engager adapted to cooperate with and mate to the receiver; and
a shroud wherein said shroud covers at least a portion of said interchangeable surgical tool.

29. The apparatus according to claim 28, wherein the receiver further defines a generally hook shaped recess adapted to cooperate with and mate to the engager and capable of transferring rotational force from the prime mover to the tool.

30. The apparatus according to claim 28, wherein the engager is further formed with a generally hook shaped projection adapted to cooperate with and mate to the receiver and capable of transferring rotational force from the prime mover to the tool.

31. The apparatus according to claim 28, wherein the engager deforms such that the engager can no longer cooperate and mate with the receiver thereby rendering the apparatus nonfunctional when the engager is subjected to a predetermined force that is less than the force that causes failure of the prime mover, the actuator, the receiver, or the interchangeable surgical tool.

32. The apparatus according to claim 28, wherein the engager is formed with a frangible portion designed to break in an orientation substantially orthogonal to the direction of translation of the prime mover.

33. The apparatus according to claim 32, wherein the frangible portion is sealed from an exterior environment by an interface between an outer portion of the interchangeable surgical tool and the manipulation shaft.

34. The apparatus according to claim 32, wherein the frangible portion is designed to break when subjected to a predetermined force that is less than the force that causes failure of the prime mover, the actuator, the receiver, or the interchangeable surgical tool.

35. A reconfigurable surgical tool, comprising:
a surgical instrument assembly formed with a hollow manipulation shaft internally receiving a prime mover activated by an actuator located at a proximal end of the shaft;
the prime mover formed with an engager; and
an interchangeable surgical tool comprising an outer connector attachable to the hollow manipulation shaft and an inner connector;
the interchangeable surgical tool formed with a receiver formed with an engagement ledge and shelf and adapted to cooperate with and mate to the engager of the prime mover; wherein said receiver is further formed to define a generally hook shaped recess sized to non-releasably receive the engager and capable of transferring rotational force from the prime mover to the tool.

36. The apparatus according to claim 35, wherein the engager deforms such that the engager can no longer cooperate and mate with the receiver thereby rendering the apparatus nonfunctional when the engager is subjected to a predetermined force that is less than the force that causes failure of the prime mover, the actuator, the receiver, or the interchangeable surgical tool.

37. The apparatus according to claim 35, wherein the engager is formed with a frangible portion designed to break in an orientation substantially orthogonal to the direction of translation of the prime mover.

38. The apparatus according to claim 35, wherein the frangible portion is sealed from an exterior environment by an outer portion of the interchangeable surgical tool and the manipulation shaft.

* * * * *